(12) United States Patent
Altschul et al.

(10) Patent No.: US 9,366,674 B2
(45) Date of Patent: Jun. 14, 2016

(54) DEVICES AND FORMULATIONS FOR DETECTING, SCREENING AND MONITORING LEVELS OF CERTAIN CONSTITUENTS IN BODILY FLUIDS AND METHOD

(71) Applicant: Pop Test LLC, Cliffside Park, NJ (US)

(72) Inventors: Randice Lisa Altschul, Cliffside Park, NJ (US); Neil David Theise, New York, NY (US); Myron Rapkin, Indianapolis, IN (US); Rebecca O'Brien, Shell Knob, MO (US)

(73) Assignee: Pop Test LLC, Cliffside Park, NJ (US)

( * ) Notice: Subject to any disclaimer, the term of this patent is extended or adjusted under 35 U.S.C. 154(b) by 0 days.

(21) Appl. No.: 14/684,861

(22) Filed: Apr. 13, 2015

(65) Prior Publication Data

US 2015/0241433 A1  Aug. 27, 2015

Related U.S. Application Data

(60) Continuation-in-part of application No. 13/836,679, filed on Mar. 15, 2013, now Pat. No. 9,005,914, which is a continuation-in-part of application No. 13/606,299, filed on Sep. 7, 2012, now Pat. No. 8,431,386, which is a division of application No. 13/278,306, filed on Oct. 21, 2011, now Pat. No. 8,263,328.

(60) Provisional application No. 61/455,528, filed on Oct. 23, 2010, provisional application No. 61/455,531, filed on Oct. 23, 2010, provisional application No. 61/455,532, filed on Oct. 23, 2010, provisional application No. 61/462,890, filed on Feb. 9, 2011.

(51) Int. Cl.
| *G01N 33/574* | (2006.01) |
| *G01N 33/92* | (2006.01) |
| *G01N 33/66* | (2006.01) |
| *G01N 33/52* | (2006.01) |
| *C12Q 1/52* | (2006.01) |
| *G01N 33/558* | (2006.01) |
| *G01N 21/29* | (2006.01) |

(52) U.S. Cl.
CPC ............ *G01N 33/57438* (2013.01); *C12Q 1/52* (2013.01); *G01N 21/29* (2013.01); *G01N 33/52* (2013.01); *G01N 33/558* (2013.01); *G01N 33/66* (2013.01); *G01N 33/92* (2013.01); *G01N 2333/91188* (2013.01); *G01N 2800/085* (2013.01)

(58) Field of Classification Search
CPC ................................................. G01N 33/57438
See application file for complete search history.

(56) References Cited

U.S. PATENT DOCUMENTS 6,251,083 B1 * 6/2001 Yum .................. A61B 5/14514
                                                            600/309

OTHER PUBLICATIONS

Dungchai et al. Analytica Chimica Acta, 2010, 674:227-233.*
Chang et al. Clinical Chemistry, 2007, 53:4:686-692.*

* cited by examiner

*Primary Examiner* — Bin Shen
(74) *Attorney, Agent, or Firm* — Arthur Jacob

(57) ABSTRACT

A device is disclosed for conducting a non-invasive analysis of a bodily fluid to determine the presence and level of a certain constituent carried by the bodily fluid. An indicator formulation of the device changes color in response to exposure to the constituent to provide a visible indication of the presence and level of the constituent carried by the bodily fluid. A carrier substrate of the device is constructed of a material having voids providing a high void volume within the substrate. The device is made by applying a chromagen to the carrier substrate to create a chromagen-laden carrier member. Then, a selected reagent having a particular constituent-specific formulation is applied to the chromagen-laden member. The selected reagent then combines with the chromagen, thereby establishing the indicator formulation within the carrier substrate in place for reception of a sample of the bodily fluid.

10 Claims, 5 Drawing Sheets

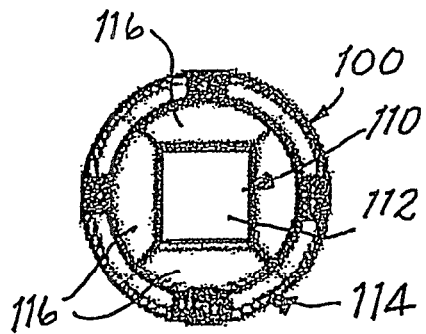
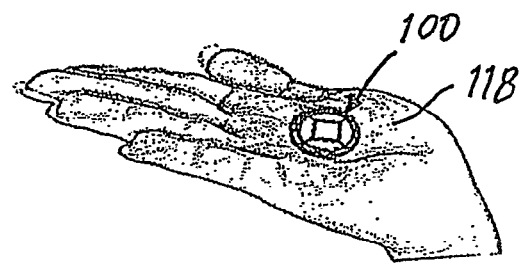
FIG. 4
FIG. 5
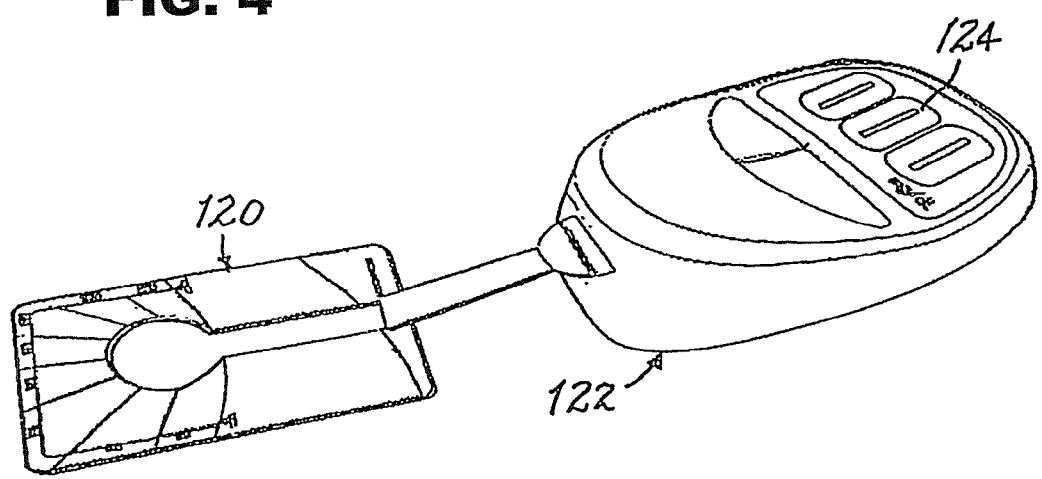
FIG. 6
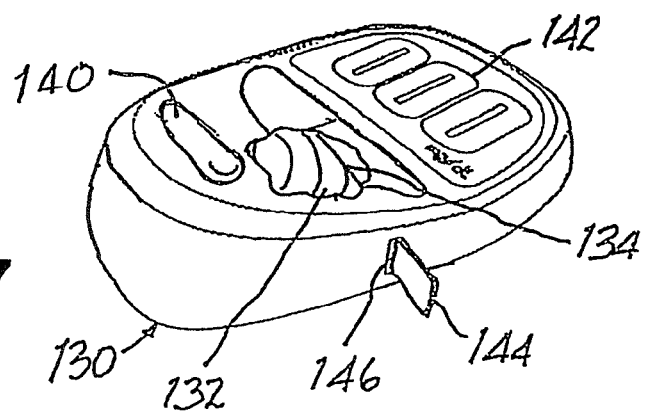
FIG. 7

DEVICES AND FORMULATIONS FOR DETECTING, SCREENING AND MONITORING LEVELS OF CERTAIN CONSTITUENTS IN BODILY FLUIDS AND METHOD

This application is a continuation-in-part of U.S. patent application Ser. No. 13/836,679, filed Mar. 15, 2013, now U.S. Pat. No. 9,005,914, which is a continuation-in-part of U.S. patent application Ser. No. 13/606,299, now U.S. Pat. No. 8,431,386, a divisional application of U.S. application Ser. No. 13/278,306, now U.S. Pat. No. 8,263,328, and further claims the benefit of U.S. Provisional Patent Application Ser. No. 61/455,528, filed Oct. 23, 2010, U.S. Provisional Patent Application Ser. No. 61/455,531, filed Oct. 23, 2010, U.S. Provisional Patent Application Ser. No. 61/455,532, filed Oct. 23, 2010, and U.S. Provisional Patent Application Ser. No. 61/462,890, filed Feb. 9, 2011, the entire disclosures of which are incorporated herein by reference thereto.

The present invention relates generally to devices and formulations for reagents employed in such devices that enable detecting, screening and monitoring levels of certain constituents in bodily fluids sampled from humans and animals, and pertains, more specifically, to the construction and manufacture of such devices.

In two earlier U.S. Pat. Nos. 7,824,344 and 7,993,283, the substance of which patents is incorporated herein by reference thereto, there is disclosed methods and apparatus for conducting a non-invasive analysis of saliva. The present invention provides formulations and devices that enable a user to employ a bodily fluid, such as saliva or another oral fluid, serum or plasma, utilizing devices that provide color changes to indicate the presence and level of a certain constituent in the bodily fluid. Further, the present invention provides methods of construction and manufacture that enable such devices to be made available for widespread use for detecting, screening or monitoring the presence and level of any one of a plurality of certain constituents with increased ease and economy. As such, the present invention attains several objects and advantages, some of which are summarized as follows: Provides devices of simplified construction for widespread use in detecting, screening and monitoring the presence and level of any selected one of a plurality of certain constituents in bodily fluids; enables an exceptionally rapid response in a quick and easy non-invasive procedure for determining the presence and level of a particular constituent in a bodily fluid; provides for the economical manufacture and distribution of devices capable of detecting, screening and monitoring the presence of certain constituents in bodily fluids; makes available a simplified visual reading of a color change to determine the presence and level of a certain constituent in a bodily fluid; provides an economical and reliable device for simplified use in detecting, screening or monitoring the presence of a selected certain constituent in a bodily fluid; encourages widespread use to the benefit of a larger number of users who can enjoy greater economy and convenience in reaching and maintaining higher goals in healthcare.

The above objects and advantages are attained by the present invention, which may be described briefly as a method of making a device for conducting a non-invasive analysis of a bodily fluid to determine the presence and the level of a certain constituent carried by the bodily fluid, the device including an indicator formulation capable of changing color in response to exposure to the certain constituent to provide a visible indication of the presence and the level of the certain constituent carried by the bodily fluid, the method comprising: providing a carrier substrate of a material having voids establishing a high void volume within the carrier substrate; applying a chromagen formulation to the carrier substrate to create a chromagen-laden carrier member; and subsequently applying to the chromagen-laden carrier member a selected reagent having a particular constituent-specific formulation to combine the selected reagent with the chromagen formulation applied to the carrier substrate, thereby establishing the indicator formulation within the carrier substrate in place for reception of a sample of the bodily fluid later placed upon the carrier substrate; wherein the different certain constituents are alanine aminotransferase (ALT) and aspartate aminotransferase (AST).

In addition, the present invention provides a device for conducting a non-invasive analysis of a bodily fluid to determine the presence and the level of a certain constituent carried by the bodily fluid, the device including an indicator formulation capable of changing color in response to exposure to the certain constituent to provide a visible indication of the presence and the level of the certain constituent carried by the bodily fluid, the device comprising: a carrier substrate of a material having voids establishing a high void volume within the carrier substrate; and an indicator formulation carried by the carrier substrate, the indicator formulation consisting essentially of a chromagen formulation and a constituent-specific formulation selected from formulations responsive to levels of either one of the certain constituents alanine aminotransferase (ALT) and aspartate aminotransferase (AST).

The present invention also provides a device for conducting a non-invasive analysis of a bodily fluid to determine the presence and the level of a selected one of the low density and high density lipoid fractions of cholesterol carried by the bodily fluid, the device including an indicator formulation capable of changing color in response to exposure to cholesterol to provide a visible indication of the presence and the level of cholesterol carried by the bodily fluid, the device comprising: at least first and second test pads, each test pad being comprised of a carrier substrate of a material having voids establishing a high void volume within the carrier substrate; an indicator formulation carried by the carrier substrate of each test pad, the indicator formulation consisting essentially of a chromagen formulation and a cholesterol-specific formulation responsive to the presence and level of cholesterol; a treatment pad juxtaposed with the second test pad; and a lipoid precipitation agent carried by the treatment pad, the lipoid precipitation agent being specific to the precipitation of one of the low density and high density lipoid fractions of cholesterol such that upon applying a sample of the bodily fluid to the first test pad a visible indication will be provided of the presence and level of cholesterol carried by the bodily fluid, and upon applying a further sample of the bodily fluid to the treatment pad, the further sample will pass through the treatment pad wherein the one of the low density and high density lipoid fractions will be removed prior to the further sample entering the second test pad to provide a visible indication of the presence and level of the other of the low density and high density lipoid fractions of cholesterol in the bodily fluid, thereby enabling a determination of the presence and level of the selected one of the low density and high density lipoid fractions present in the bodily fluid.

In addition, the present invention provides a method for conducting a non-invasive analysis of a bodily fluid to determine the presence and the level of a selected one of the low density and high density lipoid fractions of cholesterol carried by the bodily fluid, the method including the provision of an indicator formulation capable of changing color in response to exposure to cholesterol to provide a visible indication of the presence and the level of cholesterol carried by the bodily fluid, the method comprising: providing at least first and second test pads, each test pad being comprised of a carrier substrate of a material having voids establishing a high void volume within the carrier substrate; including the indicator formulation in the carrier substrate of each test pad, the indicator formulation consisting essentially of a chromagen formulation and a cholesterol-specific formulation responsive to the presence and level of cholesterol; applying a sample of the bodily fluid to the first test pad; juxtaposing a treatment pad with the second test pad; providing a lipid precipitation agent carried by the treatment pad, the lipid precipitation agent being specific to the precipitation of one of the low density and high density lipid fractions of cholesterol; applying the sample to the first test pad to derive a visible indication of the presence and level of total cholesterol carried by the bodily fluid; applying a further sample to the treatment pad wherein the one of the low density and high density lipid fractions will be removed; conducting the further sample from the treatment pad to the second test pad to derive a visible indication of the presence and level of the other of the low density and high density lipid fractions of cholesterol in the bodily fluid, thereby enabling a determination of the presence and level of the selected one of the low density and high density lipid fractions present in the bodily fluid.

Further, the present invention provides a method of screening for non-alcoholic fatty liver disease (NAFLD) in a patient, said method comprising the steps of: (a) obtaining a biological sample from a patient; (b) providing a plurality of detector devices, wherein each detector device comprises at least one detection reagent which specifically binds to an analyte, wherein the detection reagent specifically binds an analyte selected from the group consisting of glucose, cholesterol, alanine aminotransferase (ALT), and aspartate aminotransferase (AST). wherein the binding of detection reagent to analyte provides a visual indication of the presence and level of analyte in the sample, (c) applying the sample to the at least one detector device, and (d) ascertaining the presence and level of said analyte in said sample.

Still further, the present invention provides a method of screening for non-alcoholic fatty liver disease (NAFLD) in a patient, said method comprising the steps of: (a) obtaining a biological sample from a patient; (b) providing a detector device, wherein the detector device comprises a plurality of detection reagents which specifically binds to an analyte selected from the group consisting of glucose, cholesterol, alanine aminotransferase (ALT), aspartate aminotransferase (AST), and combinations thereof, wherein the binding of detection reagent to analyte provides a visual indication of the presence and level of analyte in the sample, (c) applying the sample to the detector device, and (d) ascertaining the presence and level of analyte in said sample.

In addition, the present invention provides a method of screening for liver cancer in a patient, said method comprising the steps of: (a) obtaining a biological sample from a patient; (b) providing a plurality of detector devices, wherein each detector device comprises at least one detection reagent which specifically binds to an analyte selected from the group consisting of glucose, cholesterol, alanine aminotransferase (ALT), and aspartate aminotransferase (AST), wherein the binding of detection reagent to analyte provides a visual indication of the presence and level of analyte in the sample, (c) applying the sample to the at least one detector device, and (d) ascertaining the presence and level of said analyte in said sample.

Further, the present invention provides a method of screening for liver cancer in a patient, said method comprising the steps of: (a) obtaining a biological sample from a patient; (b) providing a detector device, wherein the detector device comprises a plurality of detection reagents which specifically binds to an analyte, selected from the group consisting of glucose, cholesterol, alanine aminotransferase (ALT), aspartate aminotransferase (AST), and combinations thereof, wherein the binding of detection reagent to analyte provides a visual indication of the presence and level of analyte in the sample, (c) applying the sample to the detector device, and (d) ascertaining the presence and level of analyte in said sample.

Still further, the present invention provides a method of screening for level of low density lipoid fractions of cholesterol in a patient, said method comprising the steps of: (a) obtaining a biological sample from a patient; (b) providing a device for conducting a non-invasive analysis of a bodily fluid to determine the presence and the level of low density lipoid factions of cholesterol carried by the bodily fluid, the device including an indicator formulation capable of changing color in response to exposure to cholesterol to provide a visible indication of the presence and the level of cholesterol carried by the bodily fluid, the device comprising: at least first and second test pads, each test pad being comprised of a carrier substrate of a material having voids establishing a high void volume within the carrier substrate; an indicator formulation carried by the carrier substrate of each test pad, the indicator formulation consisting essentially of a chromagen formulation and a cholesterol-specific formulation responsive to the presence and level of cholesterol; a treatment pad juxtaposed with the second test pad; and a lipid precipitation agent carried by the treatment pad, the lipid precipitation agent being specific to the precipitation of the low density lipoid factions of cholesterol; (c) applying a sample of the bodily fluid to the first test pad a visible indication will be provided of the presence and level of cholesterol carried by the bodily fluid, and upon applying a further sample of the bodily fluid to the treatment pad, the further sample will pass through the treatment pad wherein the low density lipoid factions will be removed prior to the further sample entering the second test pad; and (d) ascertaining the presence and level of analyte in said sample, wherein the to provide a visible indication of the presence and level of high density lipoid factions of cholesterol in the bodily fluid, thereby enabling a calculation to determine the presence and level of low density lipoid factions present in the bodily fluid.

Additionally, the present invention provides A method of screening the presence and the level of low density lipoid fractions of cholesterol in a patient, said method comprising the steps of: (a) obtaining a biological sample from a patient; (b) providing a device for conducting a non-invasive analysis of a bodily fluid to determine the presence and the level of low density lipoid fractions of cholesterol carried by the bodily fluid, the device including an indicator formulation capable of changing color in response to exposure to cholesterol to provide a visible indication of the presence and the level of cholesterol carried by the bodily fluid, the device comprising: at least first and second test pads, each test pad being comprised of a carrier substrate of a material having voids establishing a high void volume within the carrier substrate; an indicator formulation carried by the carrier substrate of each test pad, the indicator formulation consisting essentially of a chromagen formulation and a cholesterol-specific formulation responsive to the presence and level of cholesterol; a treatment pad juxtaposed with the second test pad; and a lipid precipitation agent carried by the treatment pad, the lipid precipitation agent being specific to the precipitation of the low density lipoid factions of cholesterol; (c) applying a sample of the bodily fluid to the first test pad a visible indication will be provided of the presence and level of cholesterol carried by the bodily fluid, and upon applying a further sample of the bodily fluid to the treatment pad, the further sample will pass through the treatment pad wherein the low density lipoid factions will be removed prior to the further sample entering the second test pad to provide a visible indication of the presence and level of high density lipoid factions of cholesterol in the bodily fluid, thereby enabling a calculation to determine the presence and level of low density lipoid factions present in the bodily fluid; and (d) ascertaining the presence of analyte in said sample, wherein the to provide a visible indication of the presence and level of high density lipoid factions of cholesterol in the bodily fluid, thereby enabling a calculation to determine the presence and level of low density lipoid factions present in the bodily fluid.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant. Further, as used herein, the term "predetermined reference range" refers to a reference range for the particular patient, subject, or a population of subjects. Each laboratory may establish its own reference range for each particular assay, or a standard reference range for each assay may be made available and used locally, regionally, nationally, or worldwide or may be patient-specific. In one specific embodiment, the term refers to a reference range for the amount of e.g., glucose, cholesterol, alanine aminotransferase (ALT), and/or aspartate aminotransferase (AST) in a patient or a specimen from a patient. In another specific embodiment, the term refers to a reference range for the amount of e.g., glucose, cholesterol, alanine aminotransferase (ALT), and/or aspartate aminotransferase (AST) in a patient or a specimen from a patient. The assay may be run simultaneously with a second control assay wherein the control sample does not contain elevated levels of analyte. The assay may be run simultaneously with a control set of analyte standards to generate a standard curve from which sample presence and levels of analyte can be quantitated.

The invention will be understood more fully, while still further objects and advantages will become apparent, in the following detailed description of preferred embodiments of the invention illustrated in the accompanying drawing, in which:

FIG. 4 is a plan view of another device constructed in accordance with the present invention;

FIG. 5 is a pictorial view showing use of the device of FIG. 4;

FIG. 6 is a pictorial view showing the use of still another device constructed in accordance with the present invention;

FIG. 7 is a pictorial view showing the use of yet another device constructed in accordance with the present invention;

Figure 1:
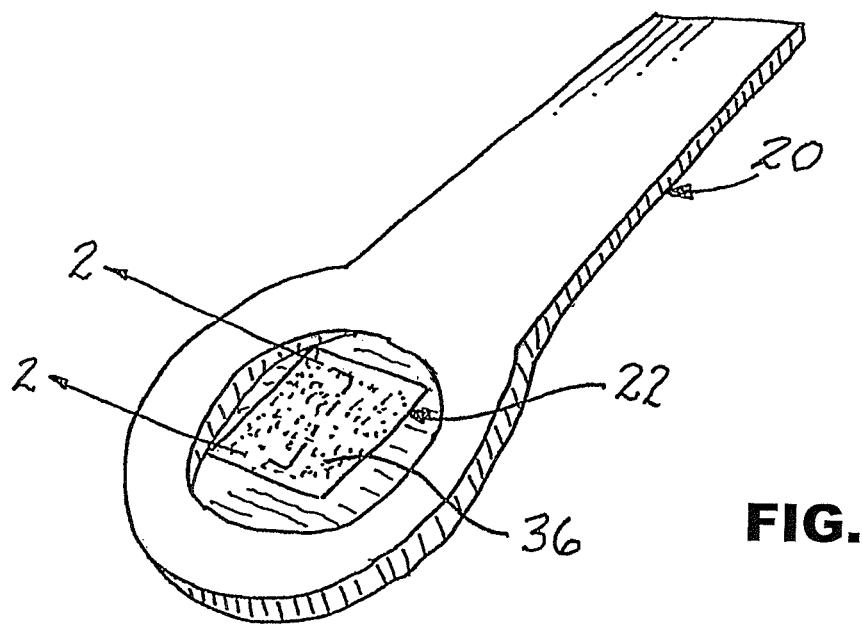
FIG. 1 is a pictorial view of a device constructed in accordance with the present invention.
Figure 2:
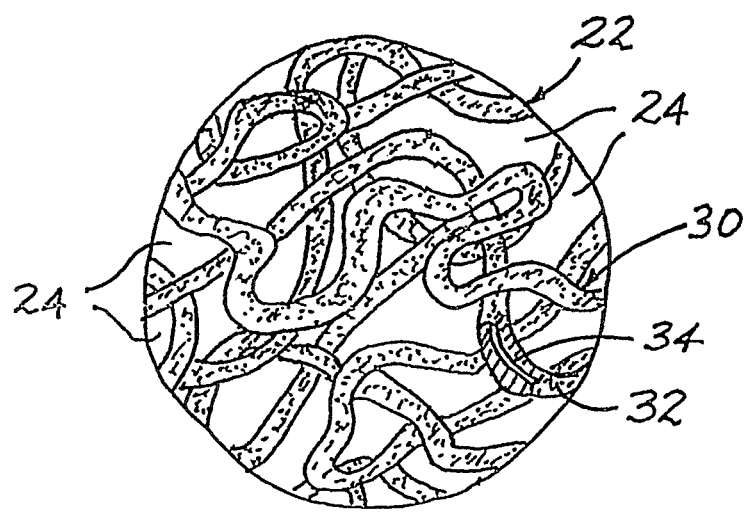
FIG. 2 is an enlarged, somewhat diagrammatic, cross-sectional view taken along line 2-2 of FIG. 1.

Referring now to the drawing, and especially to FIGS. 1 and 2 thereof, a device constructed in accordance with the present invention is shown in the form of a dry-reagent device 20 and is seen to include a carrier substrate in the form of a pad 22 of a material having voids 24 establishing a high void volume within the pad 22. An indicator formulation is carried by the pad 22 and is illustrated at 30 in the form of a layer 32 carried by fibers 34 of the material, in juxtaposition with voids 24 within the pad 22. Indicator formulation 30 consists essentially of a chromagen formulation and a reagent having a constituent-specific formulation selected from formulations responsive to one of a plurality of constituents, as will be set forth in greater detail below. Suffice it to say at this juncture that the reagent having a constituent-specific formulation and the chromagen formulation are combined within the pad 22 such that the indicator formulation 30 is capable of changing color in response to exposure to the certain constituent to provide a visible indication on the pad 22 of the presence and the level of the certain constituent carried by a sample of a bodily fluid applied to the pad 22.

Thus, upon applying a sample of a bodily fluid, such as a saliva sample, to the pad 22, placed at a target area 36 of the device 20, the occurrence of a visible color change will provide at least a qualitative indication of the presence of the particular specific constituent to which the constituent-specific formulation will react. An absence of any visible color change will indicate that the specific constituent is not present in any significant amount in the saliva sample.

The preferred material for pad 22 is a non-woven fibrous material which provides the requisite high void volume. The high void volume provides pad 22 with the ability to absorb rapidly the sample of bodily fluid applied to the target area 36, to enable rapid interaction of the sample with the indicator formulation 30, and to maximize exposure of the interacting sample and indicator formulation to ambient air for promoting a quick response through accelerating a reaction between the certain constituent carried by the sample and the indicator formulation. Non-woven synthetic polymeric materials are available commercially, one such material being a non-woven polyester fibrous material. Suitable glass-fiber non-woven fibrous materials and cellulose non-woven fibrous materials also are available commercially in forms suitable for use in the construction of pad 22. The preferred materials are chosen to provide pad 22 with a void volume within a range of about eight to twelve percent of the total volume of the material.

Device 20 is constructed in several different variations such that one variation is available to provide a visible color change as an indication of at least the presence of a corresponding one of several certain constituents, namely, ethanol, uric acid, galactose, glucose, cholesterol, alanine aminotransferase (ALT) and aspartate aminotransferase (AST) and, preferably, the level of the certain constituent, in the sample of bodily fluid applied to the target area 36 of the pad 22. Each variation requires that the pad 22 carry a formulation specific to the constituent to be detected, as a component of the indicator formulation 30; however, the chromagen formulation remains unchanged among the different variations of the pad 22 so that the same chromagen formulation can serve in every variation of the pad 22. Accordingly, the manufacture and distribution of the devices 20 is simplified and rendered more economical, as will be described below.

Figure 3:
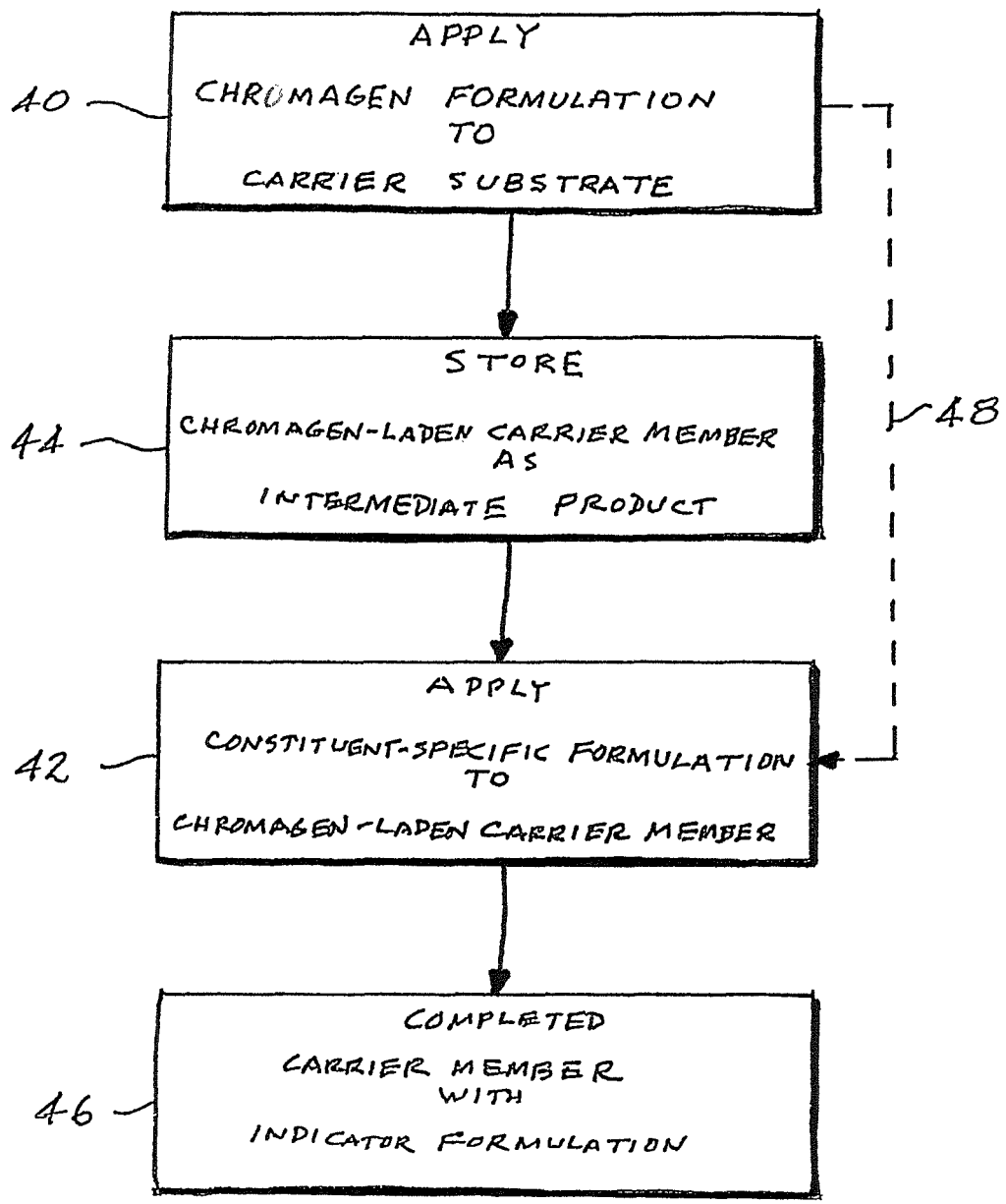
FIG. 3 is a flow diagram illustrating a method of the present invention.

Turning now to FIG. 3, as well as to FIGS. 1 and 2, pad 22 of device 20 is manufactured by first applying to the material of pad 22 the chromagen formulation, as seen in step 40, to create a chromagen-laden carrier member in the form of pad 22 with the chromagen formulation placed in juxtaposition with voids 24 of the pad 22. Subsequently, a selected reagent having a particular constituent-specific formulation is applied to the chromagen-laden carrier member, as indicated at step 42, to combine the selected reagent with the chromagen formulation applied earlier to the material of pad 22, thereby establishing the indicator formulation 30 within the completed pad 22. Pad 22 is placed at target area 36 of device 20 for reception of the sample of bodily fluid upon the pad 22. Since the chromagen formulation remains the same for all variations of the device 20, economies are realized in the manufacturing process which requires only one component common to all variations and only one station for the application of that common component; however, further economy and convenience are accomplished by the ability to store the intermediate product, that is, the material of pad 22 with the applied chromagen formulation, is stored, as seen in step 44. Subsequently, any selected one of the constituent-specific formulations is applied, at a later time, in accordance with the requirement for any number of a particular device or particular devices, the completed carrier member with the indicator formulation being available at step 46. The ability to have on hand a supply of the basic chromagen-laden carrier member for subsequent combination with a selected constituent-specific formulation, as opposed to immediately creating an inventory of completed carrier members, as indicated by procedure 48, reduces the necessity for maintaining on-hand a large inventory of every variety of completed device 20 while increasing the flexibility and turn-around time of filling the demand for any number of devices 20 in any one of the different varieties.

With respect to the varieties identified above, a preferred common chromagen formulation consists essentially of the following components, in an example prepared as follows: Approximately equal volumes of about 0.05 to 0.5 M MBTH in distilled water is mixed with about 0.05 to 0.5 M DMAB in ethanol. An alternate formulation consists essentially of approximately 500 to 1,000 mg DAOS mixed with 100 ml ethanol. The mixture is impregnated into the material of the carrier member and the impregnated material subsequently is dried, leaving the material with the chromagen formulation coated upon the fibers of the material. Other chromagen formulations compatible with the present reactions will become apparent to those persons of ordinary skill in the art.

With respect to each of the varieties identified above, the following constituent-specific formulations are effective, and an example of the preparation of each is set forth below:

For the determination of the presence and level of ethanol as the certain constituent in a bodily fluid, a constituent-specific formulation consists essentially of the following components, in an example prepared as follows: Mix together approximately equal amounts of about 1% to 20% PVP K30 in distilled water, about 0.5% to 5% ethoxylated surfactant in distilled water and about 0.05 to 0.5 M phosphate buffer at pH 8.5 together with one-half the same amount of alcohol oxidase with an activity of approximately 400 U/ml and one-quarter the same amount of peroxidase with an activity of approximately 200 U/mg. The prepared constituent-specific formulation then is impregnated into the material previously impregnated with the chromagen formulation to complete a pad 22 having an indicator formulation 30 responsive to the presence and level of ethanol in an applied sample of a bodily fluid.

For the determination of the presence and level of uric acid as the certain constituent in a bodily fluid, a constituent-specific formulation consists essentially of the following components, in an example prepared as follows: In approximately one-hundred ml of 0.05 to 0.5 M phosphate buffered saline at pH 6.4, mix together approximately ten mg of uricase, fifteen mg of ascorbate oxidase and about six mg of peroxidase with an activity of approximately 200 U/mg. The prepared constituent-specific formulation then is impregnated into the material previously impregnated with the chromagen formulation to complete a pad 22 having an indicator formulation 30 responsive to the presence and level of uric acid in an applied sample of a bodily fluid.

For the determination of the presence and level of galactose as the certain constituent in a bodily fluid, a constituent-specific formulation consists essentially of the following components, in an example prepared as follows: Mix together approximately five ml each of about 0.05 to 0.5 M phosphate buffer at pH 7.0, peroxidase with an activity of about 200 U/mg, and ethanol (95%) together with about twenty-five ml of 10% polyvinyl alcohol in distilled water and 4200 units of galactose oxidase. The prepared constituent-specific formulation then is impregnated into the material previously impregnated with the chromagen formulation to complete a pad 22 having an indicator formulation 30 responsive to the presence and level of galactose in an applied sample of a bodily fluid.

For the determination of the presence and level of glucose as the certain constituent in a bodily fluid, a constituent-specific formulation consists essentially of the following components, in an example prepared as follows: Dissolve approximately equal amounts of the enzymes glucose oxidase with an activity of approximately 200 U/mg and peroxidase with an activity of approximately 200 U/mg in distilled water in the presence of approximately equal amounts of 0.05 to 0.5 M HEPES, a blend of surface active agents within the range of about 0.1% to 10% each, and a stabilizer, the preferred stabilizer being a PVP/copolymer complex in which the copolymer is methylvinylether/maleic anhydride, available commercially under the trademark GANTREZ®, the complex being prepared from 5% PVP K30 in distilled water and 5% GANTREZ® AN 139 at a pH of about 7.5. The prepared constituent-specific formulation then is impregnated into the material previously impregnated with the chromagen formulation to complete a pad 22 having an indicator formulation 30 responsive to the presence and level of glucose in an applied sample of a bodily fluid.

For the determination of the presence and level of alanine aminotransferase (ALT) as the certain constituent in a bodily fluid, a constituent-specific formulation consists essentially of the following components, mixed together in the indicated proportions: About 100 mg of L-alanine, about 2200 units of pyruvate oxidase, about 560 mg of 4-aminoantipyrine, about 10,000 units of peroxidase, about 12,000 units of ascorbate oxidase, about 400 mg of thiamine pyrophosphate, about 640 mg of magnesium chloride and about 100 uL of 10% ON870, all mixed with about 100 ml of distilled water.

For the determination of the presence and level of aspartate aminotransferase (AST) as the certain constituent in a bodily fluid, a constituent-specific formulation consists essentially of the following components, mixed together in the indicated proportions: About 200 mg of sodium-L-aspartate, about 16 mg of a-ketoglutaric acid, about 1060 mg of oxalacetic acid decarboxylase, about 2200 units of pyruvate oxidase, about 640 mg of 4-aminoantipyrine, about 10,000 units of peroxidase, about 12,000 units of ascorbate oxidase, about 3.8 mg of thiamine pyrophosphate, about 6.4 mg of magnesium chloride and about 100 uL of 10% ON870, all mixed with about 100 ml of distilled water.

For the determination of the presence and level of cholesterol as the certain constituent in a bodily fluid, a constituent-specific formulation consists essentially of the following components, in an example prepared as follows: Dissolve approximately equal amounts of the enzymes cholesterol esterase with an activity of approximately 180 U/mg and peroxidase with an activity of approximately 200 U/mg and twice as much cholesterol oxidase with an activity of approximately 47 U/mg) in distilled water in the presence of approximately equal amounts of 0.05 to 0.5 M HEPES, a blend of surface active agents within the range of about 0.1% to 10% each and a stabilizer, the preferred stabilizer being a PVP/copolymer complex in which the copolymer is methylvinylether/maleic anhydride, available commercially under the trademark GANTREZ®, the complex being prepared from 5% PVP K30 in distilled water and 5% GANTREZ® AN 139 at a pH of about 7.5. The prepared constituent-specific formulation then is impregnated into the material previously impregnated with the chromagen formulation to complete a pad 22 having an indicator formulation 30 responsive to the presence and level of cholesterol in an applied sample of a bodily fluid.

Where it is desired further to determine the levels of both high density lipoids (HDL) and low density lipoids (LDL), in addition to providing a quantitative numeric value for total lipoids (cholesterol), the present invention provides the ability to employ dry reagent techniques, as disclosed above, lateral flow techniques, as disclosed in U.S. Pat. No. 8,889,427, or a combination of both techniques to achieve that end.

Figure 8:
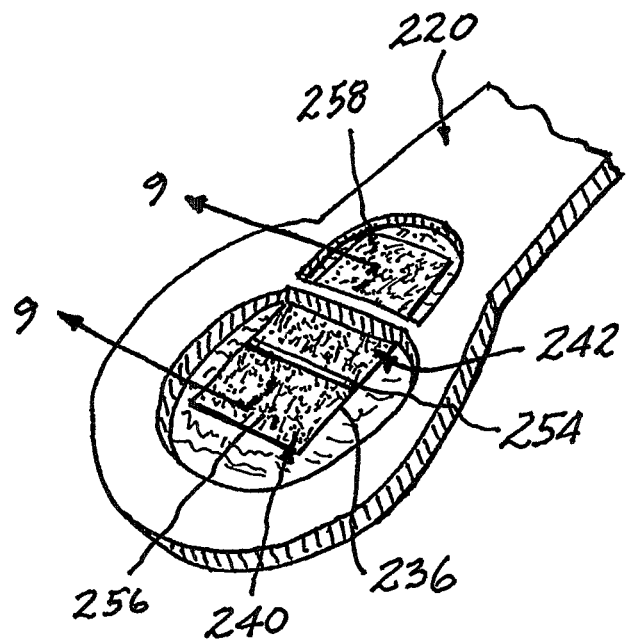
FIG. 8 is a fragmentary pictorial view of another device constructed in accordance with the present invention.
Figure 9:
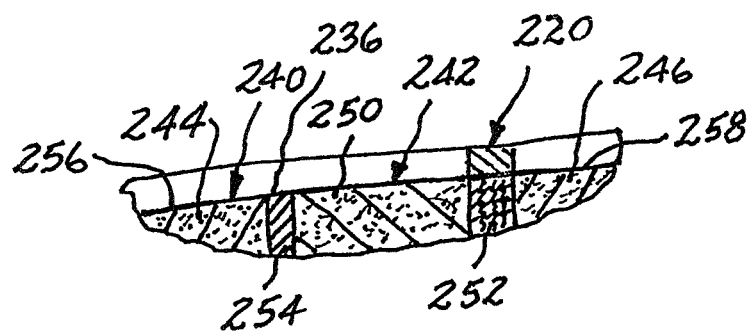
FIG. 9 is an enlarged fragmentary cross-sectional view taken along line 9-9 of FIG. 8.

Thus, for example, with reference to FIGS. 8 and 9, another device constructed in accordance with the present invention is shown in the form of a dry-reagent device 220 that includes a target area 236 having adjacent independent sections 240 and 242 placed for reception of a sample of bodily fluid, such as a saliva sample. Section 240 includes a test pad 244 constructed as described above in connection with pad 22 and carrying the constituent-specific formulation for the detection of the presence and level of cholesterol. A second test pad 246 is located remote from first test pad 244 and also is constructed as described above in connection with pad 22, carrying the constituent-specific formulation for detecting cholesterol.

Section 242 includes a treatment pad 250 that carries a lipoid precipitation agent, such as an organic acid, specific to the precipitation of the LDL fraction of cholesterol. Thus, upon applying to the target area 236 a sample of a bodily fluid, such as a saliva sample, a first portion of the sample will enter directly into test pad 244, while a second portion of the sample will enter treatment pad 250 to proceed through treatment pad 250 to test pad 246. A filter member 252 is interposed between treatment pad 250 and test pad 246 so that passage of liquid precipitation agent from treatment pad 250 into test pad 246 is precluded. Further, a barrier 254 isolates section 240 from section 242, thereby assuring that liquid precipitation agent cannot migrate from treatment pad 250 into test pad 244.

Accordingly, upon introducing a sample of bodily fluid, such as a saliva sample, to the target area 236, a portion of the sample will enter test pad 244 and a color change indicative of the total level of cholesterol present in the sample portion will appear at a surface 256 of test pad 244, while another portion of the sample will enter treatment pad 250, will pass through treatment pad 250, and will enter test pad 246, so that a color change indicative of the level of the HDL fraction of cholesterol present in the sample portion will appear at a surface 258 of the test pad 246, the LDL fraction having been removed at the treatment pad 250. These results for the levels of total cholesterol and of the HDL fraction then are used in connection with a standard algorithm to calculate the level of the LDL fraction present in the bodily fluid. Alternately, the level of the LDL fraction can be determined directly by removing the HDL fraction with an appropriate lipoid precipitation agent in the treatment pad 250 so that the color change at test pad 246 will be indicative of the level of the LDL fraction of cholesterol present in the sample portion. Should it further be desired to determine the level of very low density lipoids (VLDL) in the bodily fluid, similar separation, indication and calculation techniques can be employed.

Figure 10:
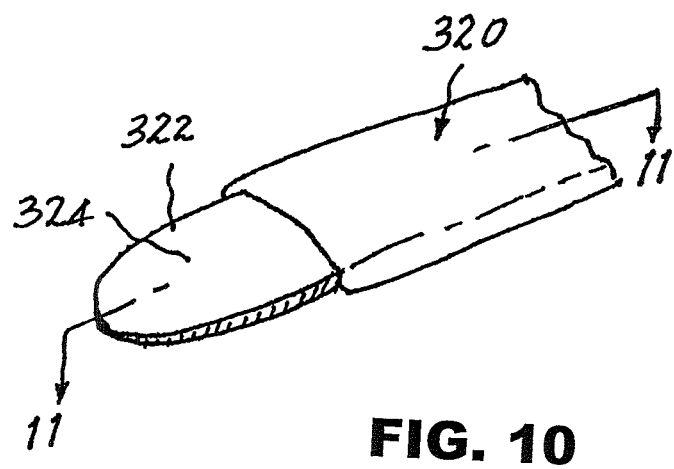
FIG. 10 is a fragmentary pictorial view of yet another device constructed in accordance with the present invention.
Figure 11:
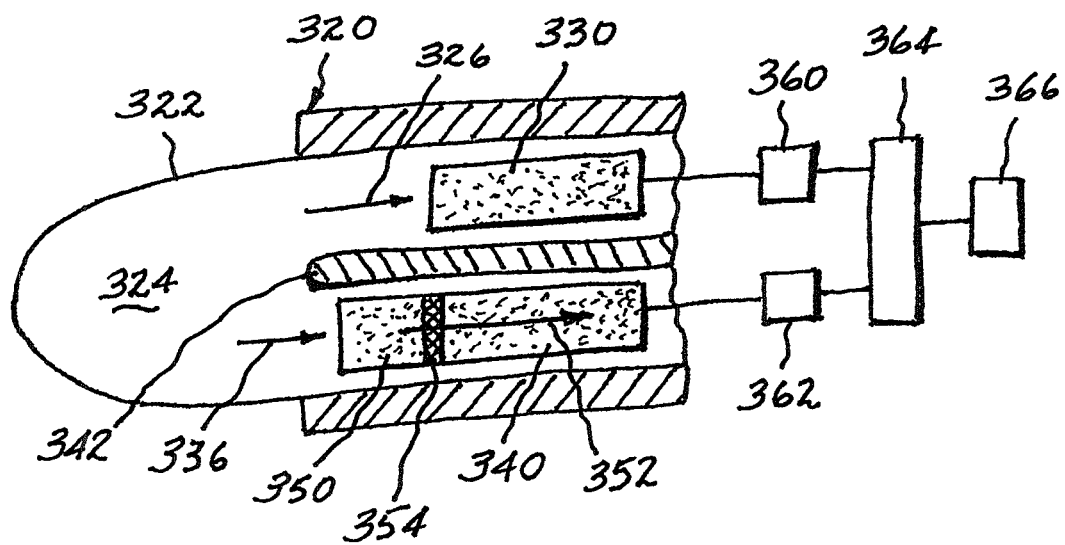
FIG. 11 is a partially diagrammatic and enlarged fragmentary cross-sectional view taken along line 11-11 of FIG. 10.

Referring now to FIGS. 10 and 11, another device constructed in accordance with the present invention is shown in the form of a lateral flow device 320, as described more fully in the aforesaid U.S. Pat. No. 8,889,427, the disclosure of which is incorporated herein by reference thereto. Device 320 includes a test strip 322 having a target area 324 placed for reception of a sample of bodily fluid, such as a saliva sample. Test strip 322 is constructed of a porous material that enables removal of a first portion of the sample laterally, as illustrated diagrammatically at 326 in FIG. 11, to a first test pad 330 which carries a constituent-specific formulation for the detection of the presence and level of cholesterol.

A second portion of the sample is moved laterally, as illustrated diagrammatically at 336, toward a second test pad 340 placed adjacent first test pad 330, the second test pad 340 being isolated from first test pad 330 by a barrier 342. Test pad 340 likewise carries the constituent-specific formulation for detecting cholesterol. A treatment pad 350 is interposed between the target area 324 and the second test pad 340, in position to receive the second portion of the sample from the target area 324. Treatment pad 350 carries a lipoid precipitation agent, such as an organic acid, specific to the precipitation of the LDL fraction of cholesterol. The second portion of the sample, now treated within treatment pad 350 to remove the LDL fraction, moves laterally, as illustrated at 352, and passes through a filter member 354 that precludes passage of the liquid precipitation agent from treatment pad 350 into test pad 340. Accordingly, as further illustrated diagrammatically in FIG. 11, upon introducing a sample of bodily fluid, such as a saliva sample, to the target area 324, a color change at test pad 330 indicative of the total level of cholesterol present in the sample will be read at 360, while a color change indicative of the level of the HDL fraction remaining after removal of the LDL fraction at treatment pad 350 will be read at 362. These results for the levels of total cholesterol and of the HDL fraction then are used in connection with a standard algorithm to calculate, at 364, the level of the LDL fraction present in the bodily fluid, which level is displayed at 366. Alternately, the level of the LDL fraction can be determined directly by removing the HDL fraction with an appropriate lipoid precipitation agent in the treatment pad 350 so that the color change at test pad 340 will be indicative of the level of the LDL fraction of cholesterol present in the sample portion.

It will be apparent that the placement of test pads 244 and 246, as well as test pads 330 and 340, can be in parallel, or in series, or in any feasible relationship adjacent to one another enabling the flow of sample material into corresponding test pads. Thus, the test pads can be on the same or on opposite sides of a test strip. Any reading of the results of a test can be made from the top side or from the bottom side of the test strip, or from both sides.

The importance of screening for the presence and level of each of the various constituents identified above is well-known. Of particular interest, however, is the ability to determine the existence of specific diseases, based upon the presence of certain combinations of these detected constituents. For example, a patient exhibiting elevated levels of ALT or AST presents a possibility of the presence of non-alcoholic fatty liver disease (NAFLD) or non-alcoholic steatohepatitis (NASH), a disease growing to epidemic proportions globally. Accordingly, upon utilization of the present invention to screen for the determination of the presence and level of certain of the herein-enumerated constituents, a patient having signs of elevated levels of cholesterol AND elevated levels of glucose, accompanied by elevated levels of ALT AND elevated levels of AST, the patient is very likely to have NAFLD or NASH. A patient having signs of elevated levels of cholesterol OR elevated levels of glucose, accompanied by elevated levels of ALT AND elevated levels of AST is likely to have NAFLD or NASH. A patient having signs of elevated levels of cholesterol AND elevated levels of glucose, accompanied by elevated levels of ALT OR elevated levels of AST, the patient is likely to have NAFLD or NASH. Thus, in summary, a patient having elevations of three or four of the markers cholesterol, glucose, ALT and AST is likely to have NAFLD or NASH, and would require further medical investigation. When screening for NAFLD or NASH, in accordance with the present invention, a biological sample can be a member selected from the group consisting of whole blood, serum, plasma, cerebrospinal fluid, saliva, urine, spinal fluid, synovial fluid, amniotic fluid and cranial fluid, and lymphocyte or cell culture supernatants. In connection with the formulations set forth above, the detection reagent can be selected from the group consisting of chromagens; antigens; haptens; monoclonal and polyclonal antibodies; natural and synthetic mono-, oligo- and polysaccharides; lectins; avidin and streptavidin; biotin; growth factors; hormones; receptor molecules; and combinations thereof.

In addition, it is noted that current indications are that NAFLD can cause primary liver cancer, in particular hepatocellular carcinoma (HCC), so reliable screening protocols for the presence of NAFLD become of even greater importance for determining populations requiring more aggressive screening for liver cancer. With respect to HCC, a notoriously chemo-resistant tumor, it is likely that further new treatments will be necessitated by such an explosion in NAFLD-associated malignancies. Addressing this possibility, glucocorticoid-receptor (GR) often is expressed in the nuclei of HCC, indicating that the tumor is likely responsive to the chemosensitizing effects of Org34517, as has already been demonstrated in xenograft models of human, GR-expressing ovarian and breast carcinomas, as set forth in U.S. Pat. No. 8,658,128.

In the embodiment of the invention illustrated in FIG. 4, a disk-shaped device 100 includes a pad 110 constructed of the material previously described in connection with pad 22 of device 20. Pad 110 provides a target area 112 which, in device 110, is substantially surrounded by an integrated color gauge 114 having patches 116 of different colors that can be matched visually with a color change at the target area 112. As in the devices disclosed in the aforesaid patents, U.S. Pat. Nos. 7,824,344 and 7,993,283, alpha-numeric characters may be displayed in juxtaposition with the patches 116 for a direct reading of the level detected. In this manner, device 100 provides a simple semi-qualitative/semi-quantitative measure of the presence and level of a particular certain constituent carried by a sample of bodily fluid applied to the target area 112. The semi-qualitative/semi-quantitative indication, while more comprehensive than the generally qualitative indication provided by device 20 described above, is convenient, as shown in FIG. 5 where the device 100 is placed readily within the palm 118 of a user's hand, but not as comprehensive as the indication provided by other embodiments of the invention, as set forth below.

In the embodiment shown in FIG. 6, a device 120 is constructed as described in detail in the aforesaid patents, U.S. Pat. Nos. 7,824,344 and 7,993,283, and is inserted into a reader 122 that employs an algorithm which converts a sensed color change into an accurate digital readout at a display 124, for a more accurate quantitative evaluation of the presence and level of a particular certain constituent carried by a bodily fluid sample.

In the embodiment illustrated in FIG. 7, a device 130 carries a strip 132 similar in construction to pad 22 described above, and arranged in a coil 134 held within the device 130. A sample of bodily fluid is applied to the strip 132, at a target area registered with an access door 140 through which the sample is passed to the strip 132. A color change is sensed and an algorithm converts the sensed color change into an accurate digital readout at a display 142. The used portion 144 of the strip 132 is advanced through a slot 146 and is torn off and discarded.

The embodiments illustrated in FIGS. 6 and 7 are conveniently available to a user wishing to control and maintain weight levels. Thus, for example, upon use of a device 120 or 130 in connection with monitoring the level of glucose in a bodily fluid, such as saliva, the algorithms provided by these embodiments can convert the detected glucose level into glycemic control readily understood and employed by a user in connection with a weight control regimen. In this manner, the user is provided with information to refine glycemic control, enabling the user to adjust diet, supplement intake and exercise for the purpose of glycemic control and weight control.

In another embodiment of the present invention, a dry-reagent device, a lateral flow device, or another test device, preferably constructed in the form of a dipstick, is incorporated into a kit suitable for home testing. A screening test, as described above, would provide convenience, privacy and eliminate the necessity and cost of visiting a physician for a screening test, although the dipstick or other test device-based kit could also be used in a clinical setting. The dipstick or other test device-based kit would be similar to a home pregnancy kit, known to those of skill in the art, and could provide a color indication of, or an increased risk for, e.g., NAFLD/NASH and the like described herein, e.g., an analyte such as glucose, cholesterol, alanine aminotransferase (ALT), and aspartate aminotransferase (AST). Such a test device-based kit could be provided with a small plastic cup for collecting and retaining the sample and for conducting the test. In one scenario, the dipstick or other test device could react to produce one color if a level of a first analyte, a different color if a level of, e.g., a second analyte is exceeded, and when both levels are exceeded, the two colors would combine to yield a third color easily distinguishable from the others.

It will be seen that the present invention attains all of the objects and advantages summarized above, namely: Provides devices of simplified construction for widespread use in detecting, screening and monitoring the presence and level of any selected one of a plurality of certain constituents in bodily fluids; enables an exceptionally rapid response in a quick and easy non-invasive procedure for determining the presence and level of a particular constituent in a bodily fluid; provides for the economical manufacture and distribution of devices capable of detecting, screening and monitoring the presence of certain constituents in bodily fluids; makes available a simplified visual reading of a color change to determine the presence and level of a certain constituent in a bodily fluid; provides an economical and reliable device for simplified use in detecting, screening or monitoring the presence of a selected certain constituent in a bodily fluid; encourages widespread use to the benefit of a larger number of users who can enjoy greater economy and convenience in reaching and maintaining higher goals in healthcare.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A method of screening for non-alcoholic fatty liver disease (NAFLD) in a patient, said method comprising the steps of:
   (a) obtaining a biological sample from the patient;
   (b) providing at least three detector devices, each detector device comprising at least one detection reagent that specifically binds to an analyte selected from the group consisting of glucose, cholesterol, alanine aminotransferase (ALT), and aspartate aminotransferase (AST), wherein the binding of the provided detection reagent to the corresponding analyte provides a visual indication of the presence and level of the corresponding analyte in the sample,
   (c) applying the biological sample to the at least three detector devices,
   (d) detecting the presence and level of each corresponding analyte in the biological sample by evaluating the visual indications, and
   (e) identifying a positive screen for NAFLD and/or non-alcoholic steatohepatitis (NASH) if elevated levels of at least three of the analytes selected from the group consisting of glucose, cholesterol, alanine aminotransferase (ALT), and aspartate aminotransferase (AST) relative to a predetermined reference range and/or control sample analyte are detected.

2. The method of claim 1 wherein the biological sample is a member selected from the group consisting of whole blood, serum, plasma, cerebrospinal fluid, saliva, urine, spinal fluid, synovial fluid, amniotic fluid and cranial fluid, and lymphocyte or cell culture supernatants.

3. The method of claim 1 wherein the at least one detection reagent of each detector device is selected from the group consisting of chromagens; antigens; haptens; monoclonal and polyclonal antibodies; natural and synthetic mono-, oligo- and polysaccharides; lectins; avidin and streptavidin; biotin; growth factors; hormones; receptor molecules; and combinations thereof.

4. The method of claim 1 wherein each detector device is a lateral flow device.

5. The method of claim 1 wherein each detector device is a dry-reagent device.

6. A method of screening for non-alcoholic fatty liver disease (NAFLD) in a patient, said method comprising the steps of:
   (a) obtaining a biological sample from the patient;
   (b) providing a detector device comprised of at least three detection reagents, each of which detection reagents specifically binds to an analyte selected from the group consisting of glucose, cholesterol, alanine aminotransferase (ALT), aspartate aminotransferase (AST), and combinations thereof, wherein the binding of the provided detection reagent to the corresponding analyte provides a visual indication of the presence and level of the corresponding analyte in the sample,
   (c) applying the biological sample to the detector device,
   (d) detecting the presence and level of each corresponding analyte in the biological sample by evaluating the visual indications, and
   (e) identifying a positive screen for NAFLD and/or non-alcoholic steatohepatitis (NASH) if elevated levels of at least three of the analytes selected from the group consisting of glucose, cholesterol, alanine aminotransferase (ALT), and aspartate aminotransferase (AST) relative to a predetermined reference range and/or control sample analyte are detected.

7. The method of claim 6 wherein each detection reagent is selected from the group consisting of chromagens; antigens; haptens; monoclonal and polyclonal antibodies; natural and synthetic mono-, oligo- and polysaccharides; lectins; avidin and streptavidin; biotin; growth factors; hormones; receptor molecules; and combinations thereof.

8. The method of claim 6 wherein the biological sample is a member selected from the group consisting of whole blood, serum, plasma, cerebrospinal fluid, saliva, urine, spinal fluid, synovial fluid, amniotic fluid and cranial fluid, and lymphocyte or cell culture supernatants.

9. The method of claim 6 wherein the detector device is a lateral flow device.

10. The method of claim 6 wherein the detector device is a dry-reagent device.

* * * * *